US010607827B2

(12) United States Patent
Taylor et al.

(10) Patent No.: US 10,607,827 B2
(45) Date of Patent: Mar. 31, 2020

(54) METHOD AND APPARATUS FOR THE CHEMICAL IONIZATION OF SAMPLES

(71) Applicant: Smiths Detection-Watford Limited, Hertfordshire (GB)

(72) Inventors: Stephen Taylor, Watford Hertfordshire (GB); Jonathan Atkinson, Watford Hertfordshire (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 29 days.

(21) Appl. No.: 15/922,377

(22) Filed: Mar. 15, 2018

(65) Prior Publication Data

US 2018/0277349 A1    Sep. 27, 2018

Related U.S. Application Data

(63) Continuation of application No. 15/329,147, filed as application No. PCT/GB2015/052116 on Jul. 22, 2015, now Pat. No. 9,953,823.

(30) Foreign Application Priority Data

Jul. 25, 2014   (GB) .................................. 1413236.9

(51) Int. Cl.
*H01J 49/14*       (2006.01)
*H01J 49/00*       (2006.01)
(Continued)

(52) U.S. Cl.
CPC .......... *H01J 49/145* (2013.01); *G01N 27/622* (2013.01); *H01J 49/0009* (2013.01);
(Continued)

(58) Field of Classification Search
CPC ............... H01J 49/0009; H01J 49/0027; H01J 49/0031; H01J 49/0072; H01J 49/10; G01N 27/622
See application file for complete search history.

(56) References Cited

U.S. PATENT DOCUMENTS 4,005,291 A * 1/1977 Arsenault ............... H01J 49/10
250/282
5,218,203 A * 6/1993 Eisele .................... G01N 27/66
250/282

(Continued)

FOREIGN PATENT DOCUMENTS

CN         1221967 A      7/1999
CN       101641593 A      2/2010
(Continued)

OTHER PUBLICATIONS

McAllster, Graeme C. et al., "Implementation of Electron-Transfer Dissociation on a Hybrid Linear Ion Trap-Orbitrap Mass Spectrometer", Anal. Chem, 2007, 79 pp. 3525-3534.
(Continued)

*Primary Examiner* — David E Smith
(74) *Attorney, Agent, or Firm* — Kevin E. West; Advent, LLP

(57) ABSTRACT

An ionising apparatus for ionising a sample of gaseous fluid. The ionising apparatus comprises an ioniser configured to provide reactant ions; an ion modifier configured to modify the reactant ions, and a reaction region arranged to receive the modified reactant ions and a sample and to combine the sample with the modified reactant ions to ionise the sample for analysis by a detector configured to identify a substance of interest in the sample.

20 Claims, 4 Drawing Sheets

(51) Int. Cl.
*H01J 49/10* (2006.01)
*G01N 27/62* (2006.01)

(52) U.S. Cl.
CPC ...... *H01J 49/0031* (2013.01); *H01J 49/0072* (2013.01); *H01J 49/10* (2013.01)

(56) References Cited

U.S. PATENT DOCUMENTS

| | | | |
|---|---|---|---|
| 5,892,364 | A | 4/1999 | Monagle |
| 6,888,132 | B1 | 5/2005 | Sheehan |
| 9,953,823 | B2 * | 4/2018 | Taylor .................. H01J 49/0031 |
| 2007/0102634 | A1 * | 5/2007 | Frey .................... H01J 49/0045 250/288 |
| 2009/0032701 | A1 * | 2/2009 | Rodier ................. G01N 27/622 250/282 |
| 2009/0084201 | A1 * | 4/2009 | Almirall ............... G01N 1/405 73/864.81 |
| 2012/0003748 | A1 | 1/2012 | Robinson et al. |
| 2012/0126109 | A1 | 5/2012 | Wu |
| 2013/0140453 | A1 | 6/2013 | Verenchikov et al. |
| 2013/0260478 | A1 * | 10/2013 | Ewing ................ G01N 33/0057 436/501 |
| 2014/0319332 | A1 | 10/2014 | Blaschke |
| 2015/0294847 | A1 | 10/2015 | Verenchikov et al. |
| 2016/0305909 | A1 * | 10/2016 | Zimmermann ....... H01J 49/061 |

FOREIGN PATENT DOCUMENTS

| | | |
|---|---|---|
| CN | 101647086 A | 2/2010 |
| CN | 101855700 A | 10/2010 |
| GB | 2515871 A | 1/2015 |
| JP | 2013541130 A | 11/2013 |
| WO | 2008107640 A1 | 9/2008 |
| WO | 2009146396 A1 | 12/2009 |
| WO | 2013072565 A1 | 5/2013 |
| WO | 2013171495 A2 | 11/2013 |

OTHER PUBLICATIONS

GB Search and Examination Report dated Feb. 6, 2015 for GB Appln. No. 1413236.9.
International Search Report dated Sep. 30, 2015 for Appln. No. PCT/GB2015/052116.
GB Search and Examination Report dated Mar. 17, 2016 for GB Appln. No. 1513190.7.
Office Action dated Sep. 8, 2017 for UK Applicatin No. GB1513190.7.
Office Action dated Mar. 5, 2018 for UK Application No. GB1800874.8.
Office Action dated Mar. 28, 2018 for CN Application No. 201580051142.3.
Office Action for Russian Patent Application No. 2017103986/07, dated Feb. 13, 2019.
Office Action for Japanese Patent Application No. 2017-504374, dated Apr. 16, 2019.

* cited by examiner

METHOD AND APPARATUS FOR THE CHEMICAL IONIZATION OF SAMPLES

Embodiments of the disclosure relate to methods and apparatus for ionisation of samples, for example samples of gaseous fluids such as gasses, vapours, and aerosols.

The influence of electromagnetic fields on ions can be used to characterise their properties. For example, in mass spectrometry an electric field can be used to accelerate ions, and the deflection of accelerated ions by a magnetic field can be used to infer their mass-to-charge ratio. In ion mobility spectrometry, ions can be moved towards a detector against a flow of drift gas, and the speed of movement of the ions can be used to draw inferences about their mobility through the drift gas. Both techniques may permit a substance of interest to be identified by analysing the influence of electromagnetic fields, such as electric and/or magnetic fields on ions, whether at ambient atmospheric pressure, or under controlled pressure conditions such as under vacuum.

The present disclosure aims to provide improved methods and apparatus for ionising a sample of a gaseous fluid for analysis by a detector. Examples of gaseous fluid include gasses and vapours.

Aspects and embodiments of the disclosure are set out in the appended claims and will now be described, by way of example only, with reference to the accompanying drawings, in which:

In the drawings like elements are used to indicate like reference numerals.

Figure 1A:
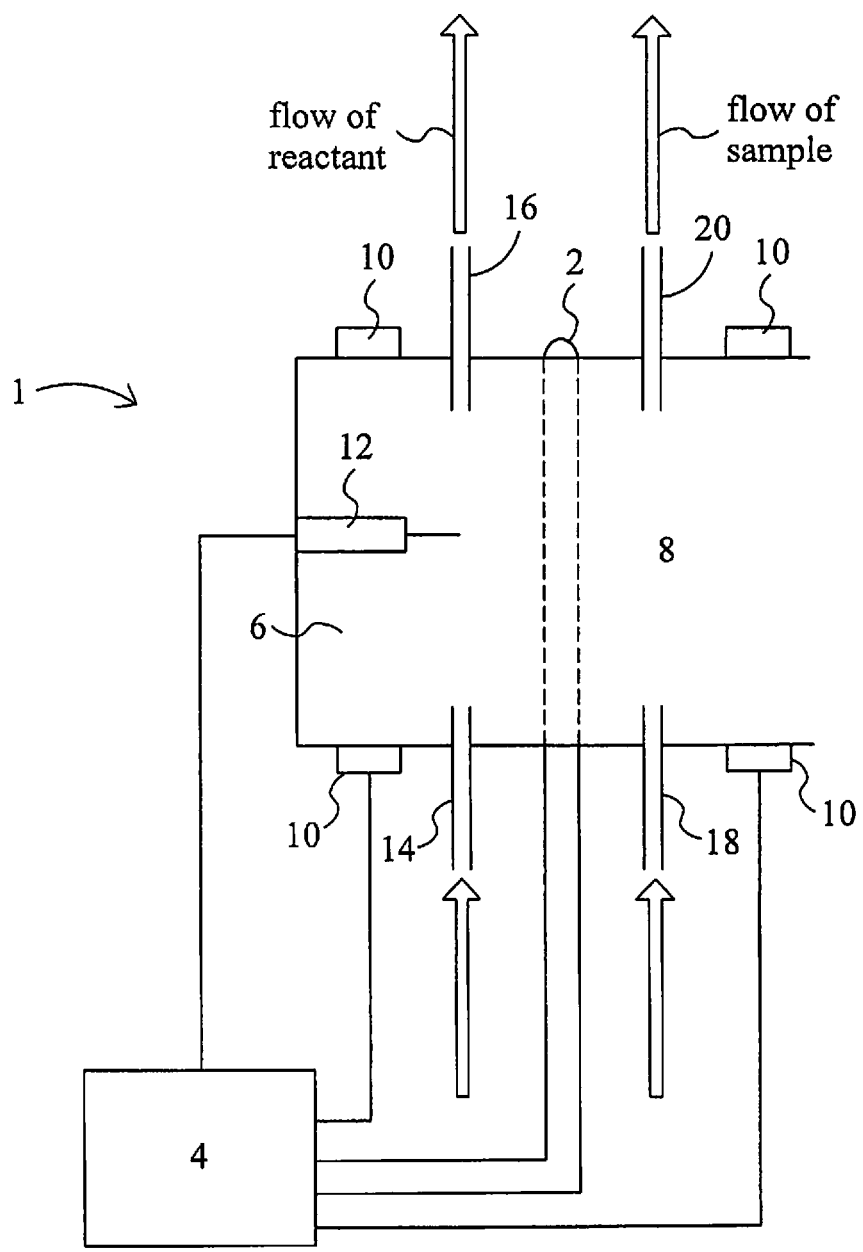
FIG. 1A shows an example of an ionising apparatus.

Embodiments of the disclosure relate to methods and apparatus in which samples of gaseous fluids are ionised by combining them with reactant ions.

Embodiments of the disclosure aim to enable a variety of different reactant ions to be provided in an ionising apparatus. These reactant ions can then be used for ionising a sample of gaseous fluid for analysis by a detector. Some types of reactant ions may interact with some types of samples to produce unwanted interferent ions which may confound analysis of the sample by the detector. In some embodiments reactant ions may be modified to suppress the production of these unwanted interferent Ions. This may therefore provide more accurate information about a sample than might otherwise be available.

One example of the disclosure is an ionising apparatus which comprises an ioniser arranged to provide reactant ions, for example by ionising a gaseous fluid such as air and/or a dopant. This apparatus also comprises an ion modifier configured to modify the reactant ions before a sample of gaseous fluid is combined with the modified reactant ions to ionise the sample. By selecting whether or not to modify the reactant ions, the type of reactant ions that are mixed with the sample can be changed. This may enable the production of unwanted interferent ions to be suppressed, or different, selected, types of product ions to be obtained from samples of the same gaseous fluid.

Different techniques may be used to ionise samples for analysis in such detectors. Ultraviolet light may be used to ionise a sample directly. More usually, sample is ionised indirectly by first generating ions from the air within the detector using corona discharge and sources of ionising radiation, such as $_\beta$-particles, and then mixing these ions with the sample to allow these ions to undergo ion-molecule reactions with the sample molecules. In this situation the initial ions generated are called reactant ions, and the ions produced from the sample molecules are called product ions. It may also be useful to add a vapour, called a dopant, to the detector, such that these become ionised by the initial air ions, and then these new reactant ions ionise the sample via ion-molecule reactions. In this way, the chemistry of the ionisation of the sample may be controlled to preferentially ionise the compounds to be detected and to not ionise some potential interferent compounds in the sample. This may enable substances whose ions may otherwise be difficult to distinguish from one another to be identified.

In an embodiment ions are produced in a reactant ion producing region and an electric field is arranged to pass them through an ion modification region and then into a reaction region into which sample is administered. A flow of dopant vapour may be administered to the reactant ion producing region and a flow not containing dopant vapour may be configured to move dopant vapour away from the modification region, so that the concentration of dopant vapour in the modification region is reduced relative to the concentration of dopant in the reactant ion producing region. The modification region is sited between the flow of dopant into the reactant ion producing region and the flow of sample into the reaction region. In an embodiment an electric field is arranged to move reactant ions, and/or modified reactant ions, into a sample in a reaction region. An ion gate may be provided to control the flow of product ions from the reaction region.

Embodiments of the disclosure also provide detection apparatus for detecting a substance of interest. The detection apparatus may comprise an ionising apparatus as described above configured to ionise a sample to provide product ions for a detector.

The detector may comprise an ion mobility spectrometer and/or a mass spectrometer.

In an embodiment the apparatus is configured to produce reactant ions, and to modify the reactant ions before combining the modified reactant ions with a sample to produce product ions for analysis by the detector.

In an embodiment the apparatus can be controlled to combine a sample with reactant ions to produce first product ions, and to analyse the sample based on providing these first product ions to the detector. The apparatus can then be controlled to obtain reactant ions, and to modify the reactant ions before combining the modified reactant ions with the sample to produce second product ions. The modified reactant ions may be different from the reactant ions, for example they may have different constituent parts, for example different mass, or different chemical properties, for example different energetic properties. The ion modifier may be operated selectively, for example the ion modifier may be operated to modify reactant ions based on a detector signal obtained from combining the first reactant ions with the sample. In some embodiments a second ion modifier may be provided and arranged for modifying product ions.

FIG. 1A shows an ionising apparatus 1. The ionising apparatus 1 includes a reactant ion producing region 6, an ion modifier 2, and a reaction region 8.

The reactant ion producing region 6 may comprise an ioniser 12, and a first inlet 14 for introducing dopant vapour, and may comprise a first outlet 16. In the example illustrated in FIG. 1A the ion modifier 2 is arranged to separate the ioniser 12 from the reaction region 8. The reaction region 8 comprises a second inlet 18 for introducing a sample to the reaction region, and may comprise a second outlet 20.

As illustrated in FIG. 1A, a controller 4 is coupled to the ioniser 12, and the ion modifier 2, and to an electric field applier 10 arranged to apply an electric field for moving ions from the ioniser 12 towards the ion modifier 2.

The ioniser 12 may be operable to apply ionising energy to form reactant ions in the reactant ion producing region 6, for example where the reactant ion producing region comprises a first inlet for introducing a dopant the ioniser may produce reactant ions by ionising the dopant, where dopant is not used the ioniser may produce reactant ions by ionising air. In some embodiments the ioniser 12 comprises a corona discharge ioniser 12, the ioniser 12 may also comprise a radioactive source of ionising radiation such as $_\beta$-particles.

The ion modifier 2 may be configured to fragment ions, for example by raising their effective temperature, for example by heating the ions and/or by subjecting them to an alternating electric field, for example a radio frequency, RF, electric field. In some examples the ion modifier 2 comprises two electrodes. The region between the ion modifier 2 electrodes may provide an ion modification region arranged so that, in order to move from the reactant ion producing region 6 to the reaction region 8, reactant ions pass through the ion modification region where they can be subjected to an alternating electric field. In an example the two electrodes may be spaced apart from each other in the direction of travel of ions from reactant ion producing region 6 to the reaction region 8. These electrodes may each be planar, and may each comprise a plurality of conductors, which may for example be arranged in a regular pattern such as a grid, for example a mesh. The ion modifier 2 may comprise a heater.

The second inlet 18 may be configured to pass a sample of gaseous fluid into the reaction region 8 to be ionised. The second outlet 20 may be arranged so that the sample flows out of the reaction region 8 in preference to flowing into the ion modification region.

The first inlet 14 and the outlet 16 may be configured to provide a flow of dopant, for example a gaseous fluid, through the reactant ion producing region 6. The inlet and outlet may be arranged to direct the flow of dopant around the ioniser 12, and may also be configured to direct the flow of dopant out of the outlet in preference to flowing towards the ion modifier 2.

The electric field appliers 10 may comprise electrodes arranged for applying an electric field to move reactant ions from the reactant ion producing region 6 through the ion modification region towards the reaction region 8.

In operation, a dopant, for example a gaseous fluid, can be introduced to the reactant ion producing region 6 through the first inlet 14. The controller 4 may then operate the ioniser 12 to apply ionising energy to provide reactant ions. Dopant may be carried out of the reactant ion producing region 6 in a flow of dopant flowing from the first inlet 14 to the first outlet 16. This may reduce the concentration of dopant in the ion modification region as compared to its concentration in the reactant ion production region 6. The controller 4 may control the electric field appliers 10 to move reactant ions in a direction different from this doped flow, for example transverse to, or against, the flow by application of an electric field. In an embodiment, the flow of dopant is selected to reduce the number of ions formed from the modified reactant ions combining with the dopant to less than a selected threshold level. One way to do this is described in more detail below.

The controller 4 may then operate the ion modifier 2 to apply energy, for example an alternating electric field and/or heat. This may raise the effective temperature of the reactant ions in the ion modification region. This may modify the reactant ions by fragmenting them and/or by separating adduct reactant ions. The controller 4 may select whether or not to operate the ion modifier 2 so as to provide either modified or unmodified reactant ions.

The modified or unmodified reactant ions may then be moved from the ion modification region into the reaction region 8 where they are combined with a sample of gaseous fluid to ionise the sample to produce product ions.

As will be appreciated in the context of the present disclosure, by selecting whether or not to operate the ion modifier 2 to modify the reactant ions, different types of product ions can be provided from the same type of sample fluid, and the same supply of dopant. This may have particular advantages where the product ions are to be provided to a detector for the purposes of analysing the sample fluid.

In an embodiment, ionisation apparatus such as that described with reference to FIG. 1A may allow for the production of reactant ions which may not otherwise be easily available. For instance, the inventors in the present case have found that ions, $NO2^-$ and $NO3^-$, may be difficult to produce directly from a dopant vapour, such as from nitric add (HNO3).

For example, if nitric acid vapour is ionised, an $NOx^-$ ion may be formed by dissociation in the ionization process, but this can then form an adduct with the HNO3 molecule. In an embodiment this adduct ion can be fragmented to release only the $NOx^-$ ion, which can then be moved into the reaction region 8. It should be noted that $NOx^-$ ions may be produced by other means such as a corona discharge, but the reactant ions produced are usually a mixture of $NO_2^-$, $NO_3^-$, $CO_3^-$, and $O_3^-$ ions in various amounts dependent upon the operation of the discharge (current, voltage, dimensions) and the time allowed for the accumulation of the products of the discharge in the vicinity of the discharge. This mixture of reactant ions leads to complicated analysis data—for example complex ion mobility spectra, which are difficult to interpret for the presence of the target compound in the sample. In the context of the present disclosure it will be appreciated that NOx has been used here only as an example, and of course other types of dopant may also be used.

Figure 1B:
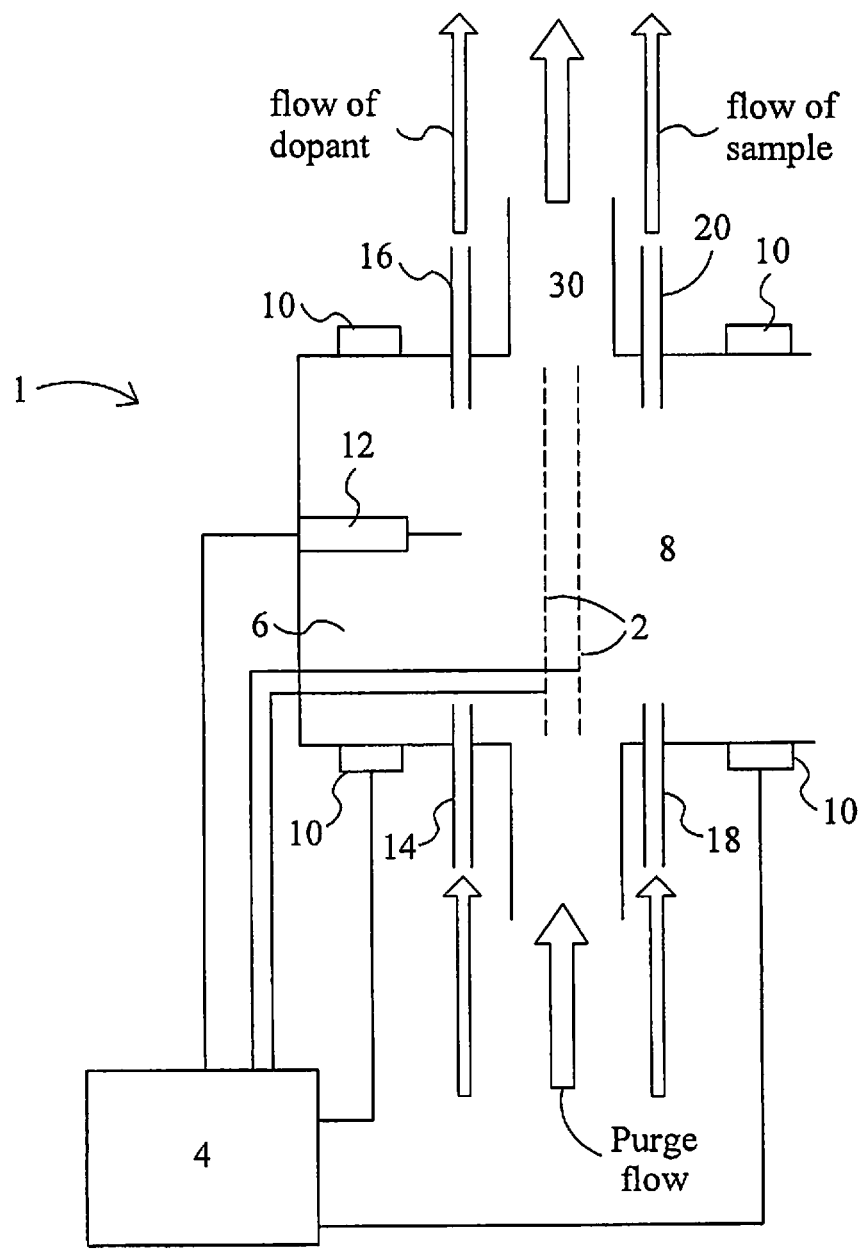
FIG. 1B shows another example of an ionising apparatus

FIG. 1 B illustrates a second ionisation apparatus. The apparatus illustrated in FIG. 1B is similar to that described above with reference to FIG. 1A. In addition however the apparatus of FIG. 1B also comprises a purge gas provider 30 arranged to provide a flow of a purge gas around the ion modifier 2. This purge gas provider 30 is configured to move neutral species, such as dopant and non-ionised sample away from the ion modifier 2 whilst permitting an electric field to move reactant ions through the ion modifier 2. This may enable reactant ions to be moved into the modification region in preference to the dopant. For example this flow of purge gas may be localised to the ion modification region, and configured to reduce the tendency of the dopant (and the sample) to enter the ion modification region, e.g. by displacing it and/or carrying it away, for example the purge gas provider 30 may comprise an inlet and an outlet arranged to provide a flow of purge gas across the ion modifier 2.

Figure 2:
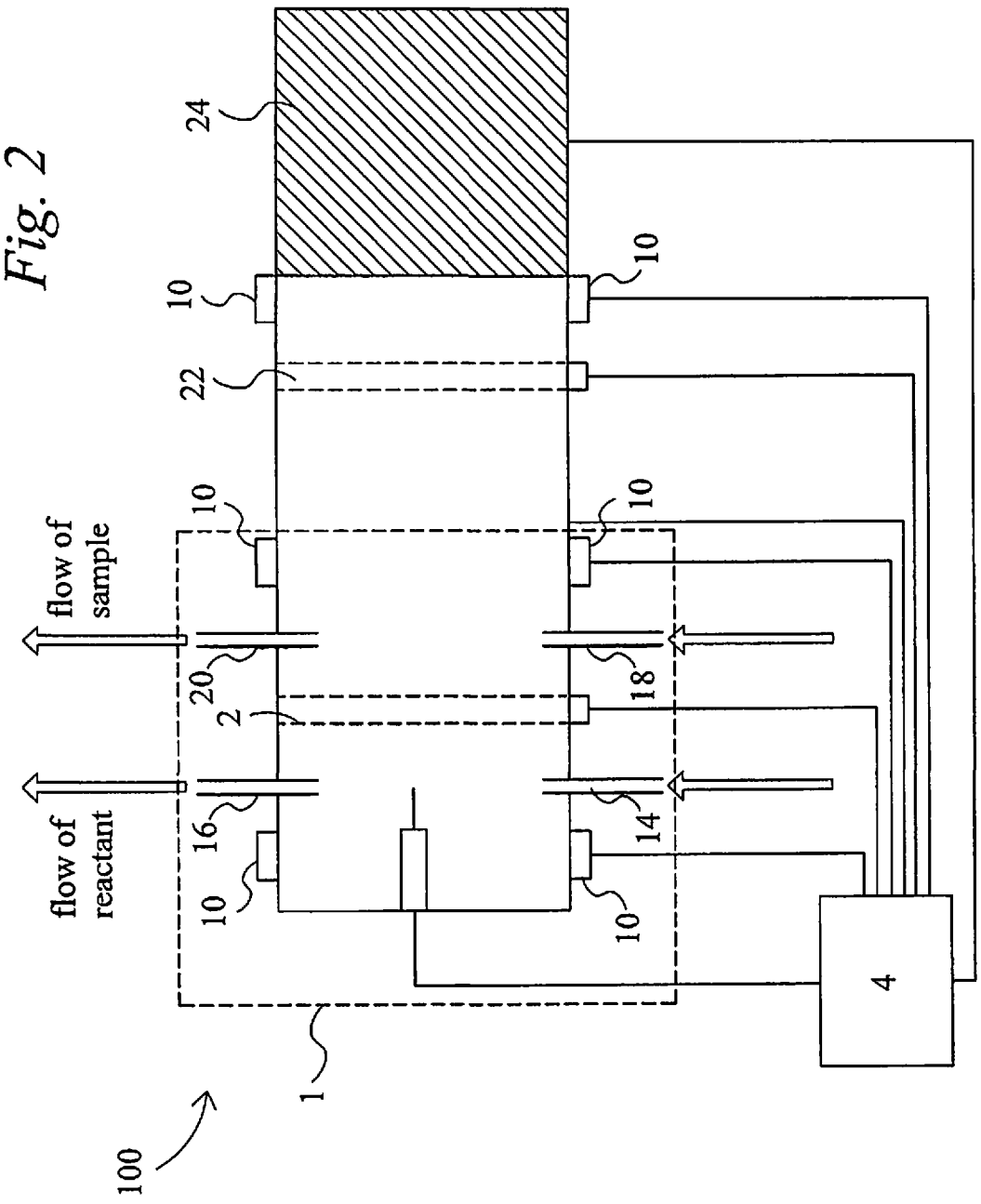
FIG. 2 shows an example of a detector comprising an ionising apparatus.

FIG. 2 shows one example of a detection apparatus 100 comprising an ionising apparatus 1, such as the ionising apparatus 1 described above with reference to FIG. 1A, or FIG. 1B a controller 4, and a detector 24. As described above with reference to FIG. 1A, the ionising apparatus 1 shown in FIG. 2 may comprise a reactant ion producing region 6, an ion modification region, and a reaction region 8. In the example illustrated in FIG. 2, the detector 24 is coupled to the ionising apparatus 1 via the reaction region 8. An ion gate may be arranged between the reaction region 8 and the detector 24, and a second ion modifier 22 may be arranged between the ion gate and the detector 24. The electric field appliers 10 shown in FIG. 2 may also be arranged to move product ions from the reaction region 8 toward the detector 24.

The controller 4 shown in FIG. 2 may be coupled to the ionising apparatus 1 in the same manner as the controller 4 described above with reference to FIG. 1A. In addition, the controller 4 illustrated in FIG. 2 may be coupled to the ion gate, the second ion modifier 22, and the detector 24.

As with the ion modifier 2 of the ionising apparatus 1, the second ion modifier 22 may comprise two electrodes which may be spaced apart to provide an ion modification region between them. The two electrodes may be arranged so that product ions pass through the ion modification region to reach the detector 24. In an example the two electrodes may be spaced apart from each other in the direction of travel of ions from the reaction region 8 to the detector 24. These electrodes may each be planar, and may each comprise a plurality of conductors, which may for example be arranged in a regular pattern such as a grid, for example a mesh. The second ion modifier 22 may comprise a heater.

The ion gate may comprise a plurality of conductors spaced apart and arranged for providing an electric field to inhibit ions from moving from the reaction region 8 to the detector 24. For example, the ion gate may comprise interdigitated conductors, which may for example be arranged in a coplanar configuration. In some embodiments conductors of the ion gate may be offset from each other in the direction of travel of the ions from the reaction region to the detector, for example the ion gate may comprise a Tyndall-Powell gate. The ion gate is operable to control the passage of product ions from the reaction region 8 toward the detector 24. The conductors of the ion gate may be arranged such that, when the conductors are at different electrical potentials, ions cannot pass through the gate. However when the conductors are at the same electrical potential, ions which do not strike the conductors can pass through the gate. The ion gate may be arranged to provide a Bradbury-Nielsen gate.

The second ion modifier 22 is operable to modify the product ions, for example by fragmenting them, for example by raising their effective temperature, for example by heating them and/or subjecting them to an alternating electric field.

The detector 24 is configured to receive the product ions and may further analyse the product ions to identify substances of interest, for example based on the interaction of the product ions with electromagnetic fields, for example electric fields and/or magnetic fields. The detector 24 may be configured to provide a signal to the controller 4 based on its analysis of the product ions. In some embodiments the detector 24 comprises the ion collector of an ion mobility spectrometer, in some embodiments the detector 24 comprises a mass spectrometer. Other types of detectors may also be used.

The controller 4 is operable to control the ionisation apparatus to obtain product ions from a sample of gaseous fluid as described above with reference to FIG. 1A. The controller 4 is further operable to determine whether or not to modify the reactant ions, and in the event that it determines that the reactant ions are to be modified, to control the ion modifier to modify the reactant ions before they are combined with the sample. The controller 4 may be operable to determine whether or not to modify the reactant ions One method of the present disclosure will now be described with reference to FIG. 3.

Figure 3:
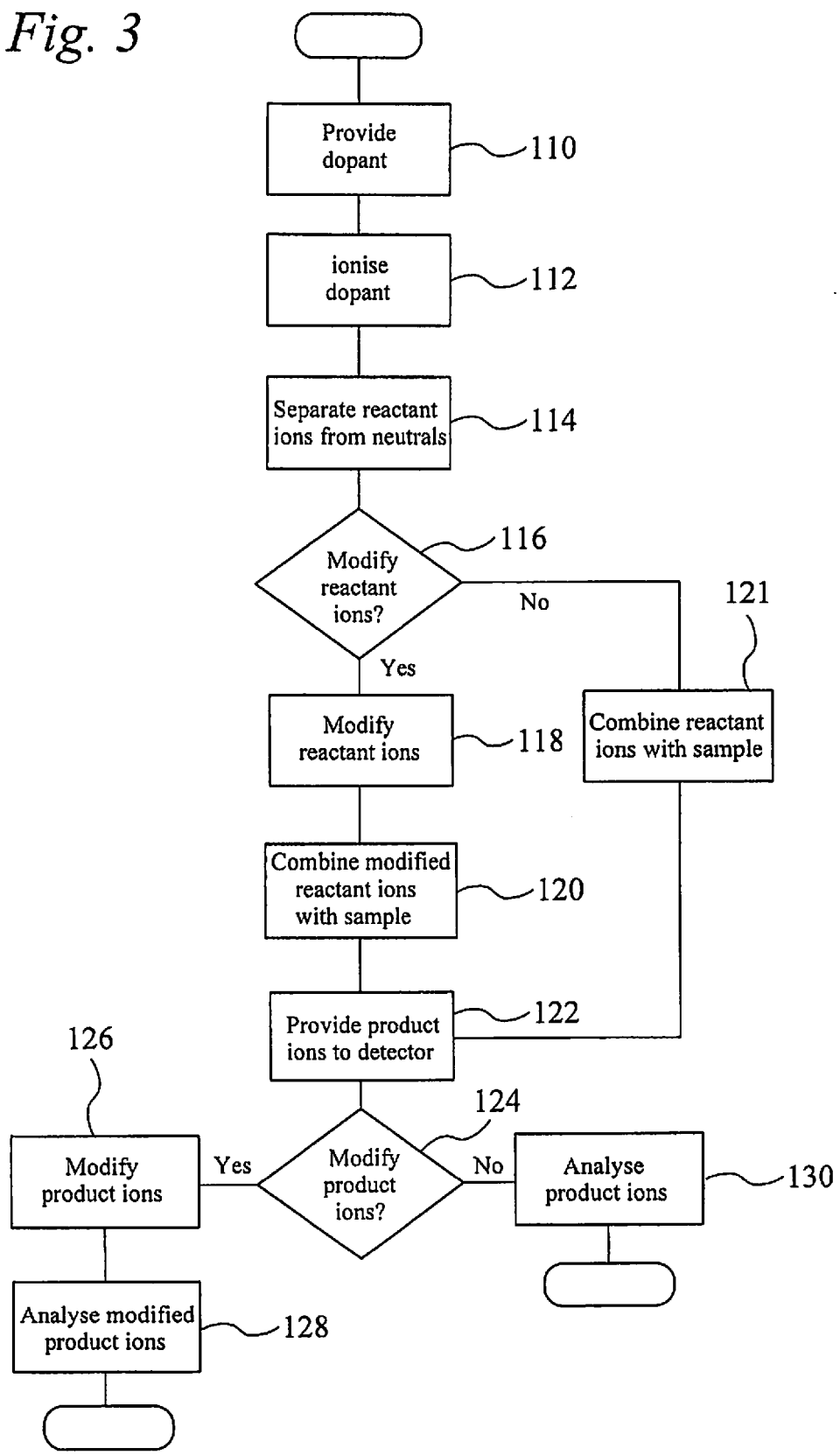
FIG. 3 shows a flow chart illustrating a method of operation of the apparatus of FIG. 2.

As illustrated in FIG. 3, a dopant may be provided 110, and ionised 112 to provide reactant ions. Dopant may then be at least partially separated 114 from the reactant ions, to reduce the concentration of dopant in the ion modification region relative to its concentration in the reactant ion producing region. A selection 116 may then be made as to whether to modify the reactant ions. If so, the reactant ions are modified 118, for example by fragmenting them, for example by raising their effective temperature. The modified reactant ions (or the unmodified reactant ions as the case may be) can then be combined 120 with a sample of gaseous fluid to ionise the sample to provide product ions.

The product ions can then be provided 122 to a detector, and a selection 124 can then be made as to whether or not to modify the product ions. If so, the product ions are modified 126, for example by fragmenting them, for example by raising their effective temperature. The modified, or unmodified, product ions can then be analysed 128, 130 by the detector.

In some embodiments the apparatus is configured to move reactant ions in to the modification region in preference to the dopant. For example, as noted above, the flow of dopant through the reactant ion producing region may be selected to inhibit the passage of dopant from the reactant ion producing region to the ion modifier. For example the volume flow rate through at least one of the first inlet 14, and the first outlet 16 may be selected to achieve this. One way this might be done is to select the cross-sectional shape or area of the first inlet 14 or the first outlet 16 to direct flow of dopant. In some examples the first inlet 14 and/or the first outlet 16 are configured to direct the flow of dopant along a path selected to inhibit the passage of dopant to the ion modifier.

In an embodiment the flow of dopant is selected so that the number of those ions formed by reaction between dopant vapour and modified reactant ions counted by the detector is less than a selected threshold level. This threshold level may be selected based on the resolution and/or signal to noise ratio of the detector. This threshold may also be selected based on routine experimentation, for example based on an experimentally determined acceptable level of modified reactant ions reacted with dopant (e.g. the system can tolerate some level of this particular ion formation and still operate correctly). For example adduct ions may comprise ions formed by reactions between dopant and reactant ions modified by the ion modifier. One way to select the flow of dopant to control the amount of dopant in the ion modification region may be based on testing for the presence of such adduct ions and adjusting the flow rate, the direction of the flows, the positioning, shape and/or size of at least one of the first inlet 14, the first outlet 16, the second inlet 18, and the second outlet 20. These parameters may be selected based on testing to achieve a sufficiently low level of adduct ion production. One way to approach this is to perform a calibration procedure. This calibration may comprise operating the apparatus to obtain a first ion mobility spectrum (e.g. a plasmagram) without introducing either the dopant or the sample. This spectrum can then be checked to see if there are any ions detected other than those expected from an undoped system (e.g. that it is "clean", and free from contamination).

This check could be made as follows:
(1) Find the dominant peak in the spectrum, and assume this is the peak formed solely by ions expected to be present in the clean system in the absence of an added dopant (examples of such ions include $O_2^-\cdot(H_2O)_n$ in the negative ion mode and $H^+\cdot(H_2O)_n$ in the positive ion mode).

(2) Determine the ion mobility constant associated with this peak and correct for temperature and pressure variations to obtain the reduced ion mobility constant, $K_0$.

(3) Determine based on the $K_0$ value whether the dominant peak is formed from ions that are expected to be present in the system in the absence of any added dopant or sample, rather than from some form of contamination.

(4) The shape of the peak may also be checked for the presence of other ion species with similar $K_0$ values to the expected ions (e.g. contaminants).

(5) Check for the presence of any other peaks in the spectrum with peak magnitudes greater than a selected level, for example a selected percentage of the dominant peak. This threshold may be selected based on the resolution of the detector and/or its signal to noise ratio. For example, the threshold may be based on the minimum resolvable peak magnitude. This threshold may also be selected based on an experimentally determined acceptable minimum level (e.g. tolerable level of contaminants).

Dopant may then be provided into the reactant ion producing region, and a second ion mobility spectrum can be obtained without introducing any sample into the reaction region. The concentration of dopant may be selected so that the "undoped" peak identified in the first ion mobility spectrum is less than a selected minimum level, for example is not detectable, in the second ion mobility spectrum, and the only peak observed is that associated ions obtained from ionising the added dopant. This selected minimum level may be based on a fraction of the magnitude of the peak height associated with the added dopant, for example 1/100th of the magnitude of that peak. An operating concentration of the additional dopant can then be determined based on the concentration of added dopant necessary to swamp the detection of "undoped" Ions in this way. The operating concentration may include an excess of additional dopant beyond that required to provide an "undoped" peak below the selected minimum level. This excess might be several fold, or even one or two orders of magnitude or more.

Having selected this concentration, calibration may further comprise selecting parameters of the flow of dopant in the reactant ion producing region. These parameters may include at least one of:

(a) the flow rate of dopant into the reactant ion producing region through the first inlet 14;

(b) the flow rate of dopant out of the reactant ion producing region through the first outlet 16;

(c) the flow path of the dopant, for example the alignment, shape, position and/or orientation of the first inlet and/or the first outlet.

Having selected these initial parameters, the calibration may further comprise obtaining a third ion mobility spectrum using the selected concentration of dopant, and these parameters, and operating the ion modifier (between the reactant ion producing region and the reaction region) to modify the reactant ions, but without introducing any sample into the reaction region.

If residual unmodified reactant ions are detected in this third ion mobility spectrum (e.g. at a level greater than the selected minimum level discussed above), it may imply that dopant is present in the ion modification region to such a concentration that some modified ions react with the dopant. It may be that the original unmodified reactant ion has been reformed from the modified ion, or another kind of ion. This has been seen in some experimentation. There may also be instances where the modified reactant ion would form a different ion species than the original doped reactant ion upon reaction with the dopant vapour. Accordingly, this third spectrum can be checked for the presence of other peaks associated with other ions, not just the presence of the doped reactant peak.

If unwanted ions (whether associated with dopant or otherwise) are detected in the ion mobility spectrum one or more of the parameters of the flow (listed above) can be varied, and additional spectra can be acquired until the level of unwanted ions reach an acceptable level (for example less than the selected minimum level discussed above).

The same calibration process may be used to select the flow of sample into the reaction region. For example parameters that control the flow of sample into the reaction region may be selected, these parameters may comprise at least one of:

(a) the flow rate of sample into the reaction region through the second inlet 18;

(b) the flow rate out of the reaction region through the second outlet 20;

(c) the flow path of the sample, for example the alignment, shape, position and/or orientation of the second inlet and/or the second outlet.

It will be appreciated in the context of the present disclosure that this calibration method may be used where the detector of the apparatus comprises an ion mobility spectrometer, and also where the detector comprises a mass spectrometer, for example a combined ion mobility spectrometer and mass spectrometer, IMS-MS, detector.

In an embodiment, to control for the possibility that ion modification may be incomplete, the ionising apparatus of the disclosure may be adapted to permit ions to be injected only into the modification region, for example within the purge gas (for example without ions being produced from dopant in the reactant ion producing region, but in the presence of the flow of dopant into the reactant ion producing region). If unwanted ions are detected it can be assumed to be from the presence of dopant in the ion modification region. An advantage of this approach is there would be no confusion with less than 100% modification efficiency: the modifier would not be operated. This scheme would have all its own problems and has been included here only to show that other test schemes could be considered.

The calibration method may be repeated under varying environmental conditions (notably temperature and pressure) and may also be repeated for each type of dopant used since concentrations of the dopants may vary with environmental conditions.

Other examples and variations of the disclosure will be apparent to the skilled addressee in the context of the present disclosure, for example, the controller 4 of the embodiments described with reference to FIG. 1A, and the embodiments described with reference to FIG. 2, may also be configured to control the timing of operation of the ioniser 12 and the ion modifier, and/or the ion gate so that their operation is synchronised, for example so that they are operated together, for example so the timing of their operation overlaps, or begins and/or ends at the same time. For example the controller 4 may be configured to operate the ioniser 12 to apply a pulse of ionising energy, and to operate the ion modifier to modify ions based on the timing of that pulse. For example, the controller 4 may be configured to control the ion modifier to apply an alternating electric field, and/or heat energy during, or to begin and/or end at the same time as the pulse applied to the ioniser 12, or at some time delayed from the operation of the ioniser. Similarly, the controller 4 may be configured to select the times at which to open the ion gate based on the timing of operation of the ioniser 12 and/or the ion modifier.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus, such as the controller, outlined herein may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. An ionising apparatus for ionising a sample of gaseous fluid, the ionising apparatus comprising:
    an ioniser configured to provide reactant ions;
    an ion modifier configured to modify the reactant ions by subjecting the reactant ions to an alternating electric field; and
    a reaction region arranged to receive the modified reactant ions and a sample and to combine the sample with the modified reactant ions to ionise the sample for analysis by a detector configured to identify a substance of interest in the sample.

2. The apparatus of claim 1, further comprising a dopant flow provider arranged to provide a flow of dopant past the ioniser, and an electric field applier arranged to move reactant ions out of the flow towards the ion modifier.

3. The apparatus of claim 1, wherein the ion modifier is arranged between the ioniser and the reaction region.

4. The apparatus of claim 1, further comprising a controller configured to operate the ioniser to produce reactant ions, and to operate the ion modifier so that the timing of the operation of the ion modifier is selected based on the timing of the operation of the ioniser.

5. The apparatus of claim 4, further comprising an ion gate arranged to control the passage of product ions out of the reaction region, wherein the controller is configured to control the timing of operation of the ion gate based on the timing of the operation of at least one of the ioniser and the ion modifier.

6. The apparatus of claim 2, wherein the dopant flow provider is configured to provide the flow of dopant in a first direction, and the electric field applier is configured to move the reactant ions in a second direction, different from the first direction, and towards the modification region.

7. The apparatus of claim 1, further comprising a purge gas provider arranged to provide a flow of purge gas across the ion modifier to provide a greater flow of purge gas to the ion modifier than to the reaction region.

8. The apparatus of claim 4, wherein the controller is configured to operate the ion modifier based on a signal from the detector.

9. The apparatus of claim 1, wherein the detector comprises at least one of an ion mobility spectrometer or a mass spectrometer.

10. A method of analysing a sample, the method comprising:
    ionising the sample, via an ionising apparatus, the ionising apparatus configured for:
    ionising a dopant to provide reactant ions;
    modifying the reactant ions by subjecting the reactant ions to an alternating electric field;
    combining the modified reactant ions with the sample to produce product ions;
    applying an electric field to move the product ions towards a detector, and
    analysing the product ions based on the movement of the product ions towards the detector for detecting the substance of interest.

11. The method of claim 10, further comprising moving reactant ions in to the modification region in preference to the dopant.

12. The method of claim 10, wherein modifying the reactant ions comprises raising the effective temperature of the reactant ions by at least one of subjecting the reactant ions to an altering electric field, or heating the reactant ions.

13. The method of claim 10, wherein the dopant is ionised by pulses of ionising energy, and the alternating electric field is timed to be at a time delayed from that of the pulses of the ionising energy.

14. The method of claim 11, wherein moving reactant ions in to the modification region in preference to the dopant comprises moving dopant in a first direction and moving the reactant ions in a second direction towards the ion modifier, wherein the second direction is different from the first direction.

15. The method of claim 14, wherein the dopant is ionised in a reactant ion producing region, and moving the dopant in a first direction comprises providing a flow of dopant out of the reactant ion producing region.

16. The method of claim 14, wherein moving the reactant ions in the second direction comprises subjecting the reactant ions to an electric field configured to move the reactant ions towards the modification region.

17. A method of analysing a sample, the method comprising:
ionising the sample via an ionising apparatus, the ionising apparatus configured for:
ionising a dopant to provide reactant ions;
modifying the reactant ions;
combining the modified reactant ions with the sample to produce product ions;
applying an electric field to move the product ions towards a detector, and
analysing the product ions based on the movement of the product ions towards the detector for detecting the substance of interest; the method further comprising providing a flow of purge gas across the ion modifier wherein the flow of purge gas is greater in the ion modification region than in the reaction region.

18. A calibration method comprising:
providing a flow of dopant through a reactant ion producing region of an ionising apparatus for ionising a sample of gaseous fluid;
ionising the dopant to provide reactant ions;
operating an ion modifier to modify the reactant ions, wherein the ion modifier is arranged between the reactant ion producing region and a reaction region of the ionising apparatus;
determining whether unwanted ions are obtained from the ion modifier; and
adjusting the flow of dopant, based on the determination that unwanted ions are obtained, to reduce the production of unwanted ions.

19. The method of claim 18, wherein adjusting the flow of dopant comprises adjusting at least one of the flow rate of dopant into the reactant ion producing region, the flow rate of dopant out of the reactant ion producing region, or the flow path of the dopant.

20. The method of claim 19, wherein adjusting the flow path of the dopant comprises adjusting at least one of the alignment of at least one of a first inlet or a first outlet, the shape of the at least one of a first inlet or a first outlet, the position of the at least one of a first inlet or a first outlet, or the orientation of the at least one of a first inlet or a first outlet.

* * * * *